United States Patent [19]

Baker et al.

[11] 4,052,010

[45] Oct. 4, 1977

[54] SUSPENDABLE POROUS GLASS PARTICLES

[75] Inventors: Frederick G. Baker, Tyrone; David L. Eaton, Horseheads, both of N.Y.

[73] Assignee: Corning Glass Works, Corning, N.Y.

[21] Appl. No.: 447,250

[22] Filed: Mar. 1, 1974

[51] Int. Cl.$^2$ .................. B02C 23/08; B02C 23/20
[52] U.S. Cl. .................. 241/20; 23/230 B; 241/24; 252/408; 424/1.5; 424/12
[58] Field of Search .............. 252/408, 114, 303, 349; 23/230 B; 195/103.5; 241/20, 24; 424/1, 12

[56] References Cited

U.S. PATENT DOCUMENTS

| 2,214,717 | 9/1940 | Breerwood | 241/20 X |
|---|---|---|---|
| 3,361,680 | 1/1968 | Bohrer | 252/314 |
| 3,519,538 | 7/1970 | Messing et al. | 195/103.5 X |
| 3,652,761 | 3/1972 | Weetall | 195/103.5 X |

Primary Examiner—Leland A. Sebastian
Attorney, Agent, or Firm—James A. Giblin; Clinton S. Janes, Jr.; Clarence R. Patty, Jr.

[57] ABSTRACT

An aqueous suspension of porous glass particles having a closely controlled average particle size within the range of about 0.7 to about 3.0 microns. The controlled particle size porous glass particles are prepared by initially milling course porous glass particles to yield particles of about 10 microns or less, leaching those particles to remove contaminants and residues, rinsing the particles, and then mixing the particles with an aqueous solution and subjecting the mixture to at least two controlled sedimentation steps.

10 Claims, 2 Drawing Figures

SUSPENDABLE POROUS GLASS PARTICLES

BACKGROUND OF THE INVENTION

1. Field

This invention relates generally to porous glass particles and specifically to an aqueous suspension of porous glass particles having a closely controlled average particle size, the suspension being especially useful in the field of solid phase radioimmunoassay.

2. Prior Art

Porous glass refers to glass which contains an intricate network of minute interconnected voids and channels. Such glass is made by first forming a body of phase-separable glass within a certain compositional range, subjecting the formed glass to a controlled heat treatment to separate it into two phases, only one of which is acid soluble, and subsequently dissolving out the soluble phase with appropriate reagents to produce the void space within the glass. The average pore diameter of the interconnected channels is commonly very small and measured in Angstrom Units (A). The ultimate pore size depends on such factors as initial glass composition, heat treatment duration and temperature, and soluble-phase separation techniques. The actual preparation of porous glass bodies is described more fully in U.S. Pat. No. 2,106,744, issued to Hood and Nordberg. Various techniques for enlarging the pores of porous glass are described in U.S. Pat. No. 3,485,687, issued to Chapman et al and U.S. Pat. No. 3,549,524, issued to Haller. A technique for preparing porous glass particles having two essentially distinct zones of porosity is disclosed in U.S. Pat. No. 3,790,475. By following specific teachings of the above disclosures, it is possible to closely control the average pore diameter of the porous glass bodies such that (e.g. U.S. Pat. No. 3,549,524), as much as 95% of the total pore volume consists of "pores" having an average pore diameter within ±20% or better. Such glass is commonly referred to as controlled pore glass or, simply, CPG. CPG can be readily prepared having an average pore diameter within the range of about 30 A to about 2500 A and is available commercially in a form having a variety of average pore diameters. The particle sizes of such porous glasses is generally in the range of about 40 to 400 mesh, U.S. Standard Sieve.

Most porous glass consists of at least about 96% silica, about 3% $B_2O_3$, and small amounts of other ingredients (e.g. Corning Code 7403, 7417, or 7930 porous glass). Because of many desirable physical and chemical properties (inertness, relatively small average pore diameter, high surface area per gram, and chemical composition), porous glass has been found useful in chromotographic applications (e.g. U.S. Pat. No. 3,114,692) and, more recently, as a carrier material for such biologically active materials as enzymes (e.g. U.S. Pat. No. 3,519,538) and antibodies (e.g. U.S. Pat. No. 3,652,761). In U.S. Pat. No. 3,652,761, there are disclosed various techniques for chemically coupling specific antibodies through intermediate silane coupling agents to porous glass particles in such a manner that the attached antibody retains its ability to complex with a specific antigen. Thus, by reacting such immobilized antibodies with a solution containing antigens specific to the antibody, it has been found possible to isolate or separate a given antigen from a solution containing other substances. Inasmuch as the complexing of a given antigen with an antibody to that antigen is a very specific reaction, the use of an immobilized antibody permits the extraction of substances having a very low concentration.

In recent years, there has been a growing recognition of the need to know concentrations of various substances which often exist in quantities as low as nanograms per ml of a solution. Since such concentrations cannot be readily determined via classical analytical methods, there has been developed a relatively new analytical method referred to as radioimmunoassay (RIA). RIA is a term used to describe a method of determining very low concentrations of substances which method is based on the use of radioactively labelled materials which can form immunochemical complexes. The RIA of a given substance for which there exists antibodies is based on the observation that an unknown amount of the given substance (unlabelled) will tend to compete equally with a known amount of that substance (labelled) for a limited number of complexing sites on antibodies specific to that substance to form immunochemical complexes of both antibody-substance (inlabelled) and antibody-substance (labelled). By separating the complexed products from the reaction solution, and then counting the radioactivity of either the separated complexes or the remaining solution, it is possible to determine the unknown concentration by relating the count to a standard curve prepared beforehand using known amounts of labelled substance.

An essential step in RIA involves separating the complexed products from the reaction solution. To facilitate the separation, it has been found highly desirable to use composites consisting of antibodies which have been immobilized on essentially water insoluble carrier materials. The use of such carriers in RIA has come to be known as solid-phase RIA or, simply, SPRIA.

The immunochemical composites described in U.S. Pat. No. 3,652,761 have been suggested as possibly useful for SPRIA. However, in attempting to use the teachings of that patent to prepare composites for SPRIA, it was found that, in many cases, it was difficult to achieve concentration measurement sensitivity in clinically significant concentration ranges. To a certain extent, that finding was surprising since some of the carriers disclosed therein (e.g. porous glass, about 500-600 A average pore diameter) had relatively high surface areas per gram, thus assuring the loading of relatively large amounts of antibody which should have permitted a fairly high degree of sensitivity. It was subsequently found that carrier particle size plays an important role in allowing a highly sensitive SPRIA and we have been able to prepare a suspension of suspendable porous glass particles having a very closely controlled particle size range which is ideally suited for use in SPRIA.

SUMMARY OF INVENTION

Our suspension of porous glass particles has been found very suitable for immobilizing antibodies to produce immobilized antibodies which can be used in the SPRIA of numerous substances. Very briefly, our suspension consists of an aqueous suspension of porous glass particles having a very closely controlled average particle size within the range of about 0.7 to about 3.0 microns, preferably within the range of about 0.7 to about 1.7 microns. The particles are formed by milling a porous glass body(ies) to a particle size of less than about 10 microns, leaching the particles to remove conaminants and residues, washing the particles, and then subjecting the particles to at least two successive and critical sedimentation or centrifugation steps from solutions to isolate closely controlled porous glass particles within the range of 0.7 to about 3.0 microns, preferably within the range of 0.7 to about 1.7 microns. The closely controlled particles are then mixed with water (e.g. sonication) to form an aqueous suspension of the porous glass particles which can then be silanized for chemical coupling of antibodies to form suspendable composites useful in SPRIA.

SPECIFIC EMBODIMENTS

Figure 1:
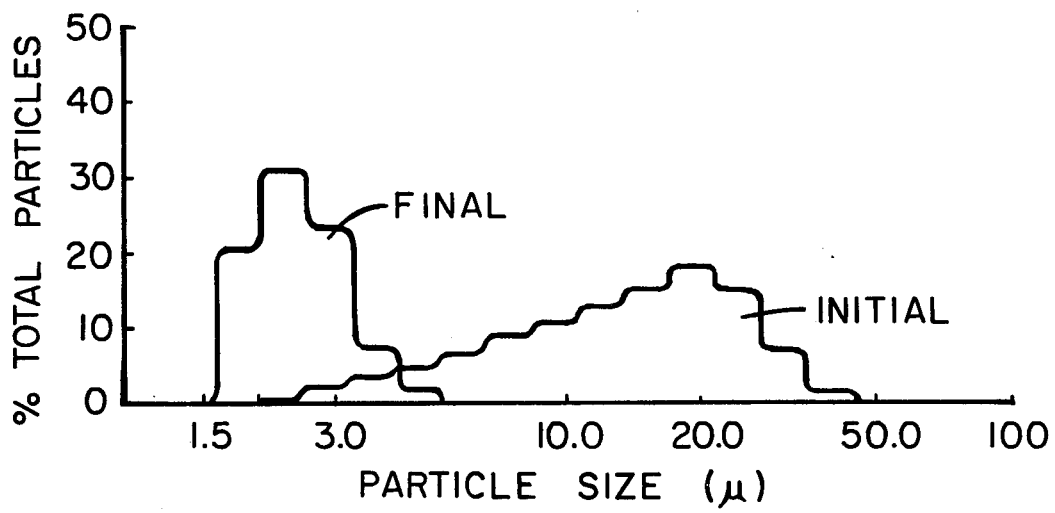
FIGS. 1-2 illustrate comparisons of particle size distributions for porous glass samples prepared in accordance with the teachings herein and porous glass samples which were merely milled.

A very critical feature of our suspension is the close control of the particle sizes of the porous glass particles and the method for preparing porous glass particles within a very critical particle size range. In using porous glass as an antibody carrier in SPRIA, it has been shown that carrier particle size is very important. See, for example, U.S. patent application Ser. No. 447,252, now U.S. Pat. No. 3,975,511 filed of even date in the names of W. Vann and S. Yaverbaum, entitled "Solid Phase Radioimmunoassay," and assigned to the present assignee. Since an accurate SPRIA requires complete separation of all complexed products prior to counting, it has been found that the carrier particle size should not exceed about 10 microns, very preferably, less than about 3.0 microns, so that the carrier-antibody composite will remain suspended in solution for a period of time to allow complexing with the labelled and unlabelled substances. Composites having carrier particle sizes above about 10 microns tend to settle relatively rapidly in solution, thus limiting the ability to draw uniform aliquots of the suspension over reasonable periods of time. Further the very size of particles beyond 10 microns can limit the diffusion of the antigen deeply into the pores thereby not fully utilizing the bonded antibodies within the pores of the porous glass. The average pore diameter of porous glass can be readily controlled, and it has been found that for most SPRIA applications the porous glass particles should have an average pore diameter within the range of about 100 A to about 1200 A. The lower pore size is dictated by antibody and/or antigen size. The higher pore size is dictated by minimum surface area requirements for maximum antibody loading per gram of carrier. For antibody loading, the surface area should be at least above 10 m²/g, very preferably at least about 20 m²/g. Utilizing this same consideration of surface area requirements with respect to non-porous particles, it is evident from the table shown below that such non-porous particles would have to be less than about 0.7 micron in average particle diameter to satisfy the preferred minimum surface area requirement.

Table I

| Avg. Particle Dia. ($\mu$) | Avg. External Surface Area(m²/g) |
| --- | --- |
| 10 | 1.4 |
| 1.0 | 13.9 |
| 0.7 | 19.8 |
| 0.5 | 27.7 |
| 0.25 | 55.4 |
| 0.1 | 138.6 |

Thus, in the very preferred particle range of 0.7 to about 3.0$\mu$, it is necessary to use a porous particle to achieve maximum antibody activity (loading).

From overall considerations, it can be seen that a suitable porous glass carrier for SPRIA is limited by interrelated parameters of pore size, surface area, and, most importantly, particle size. To assure that all complexed products are in fact separated, the lower particle size for the carrier must be such that it can be readily separated from solution with available centrifuging equipment. As a practical matter, it has been found that the antibody carrier particle size should not be smaller than about 0.7 micron lest complexed products fail to centrifuge out with available equipment, thus resulting in erroneous radioactivity counts in SPRIA which affect accuracy of concentration determinations.

Our suspension of porous glass particles meets the requirements for preparing immobilized antibodies which can be used successfully for sensitive and accurate SPRIA. The particles are prepared by using conventional ball milling or vibratory milling techniques to reduce commercially available porous glass particles (e.g. Corning Code 7407 porous glass, 40 to 80 mesh, U.S. Standard Sieve) to particles of uncontrolled particle sizes of less than 10 microns. These particles, in an aqueous slurry, are then acid-washed to remove any metal contaminants and residual acid-soluble ceramic or glass phases. Then, the particles are washed in deionized water to remove the acid residues and any silica gel residues. The washing steps are very important to assure that when the porous glass particles are subsequently silanized, and antibodies are attached, the attachment is made to a firm glass substrate rather than to silica gel residues which can come off, thus releasing the antibody from the carrier.

After the washing steps, the particles are suspended in deionized or distilled water and subjected to at least two successive sedimentations (centrifugation) steps to prepare porous glass particles within the critical closely controlled particle size range. In the first centrifugation step, the particles are initially suspended by sonication in water and then centrifuged at a RCF range of 20 to 80 to assure removal of all particles $\geq 10\mu$. RCF is defined as relative centrifuge force and is used to relate the strength of the gravity field to which the particles are subjected. It is determined by the following formula: RCF = 23.38 (radius in inches of the centrifuge) (rpm/1000)². The smaller particles remain in the supernatant and are saved. These particles have an uncontrolled average particle size range of less than 10 microns. The particles are then again suspended in distilled water (e.g. by sonication) and centrifuged at an RCF value of 5,000 to 10,000 to separate particles less than about 0.7$\mu$.

The centrifuged particles are then in the closely controlled particle size range of about 0.7 to 3.0 microns. These particles are then added to distilled water to form a suspension of porous glass particles having an average particle size range of about 0.7 to about 3.0 microns, a large percentage of the particles being less than 1.7$\mu$.

In preparing such a suspension for the immobilization of antibodies for use in SPRIA, the preferred amount of suspended particles per ml of distilled water is between about 50 mg to 150 mg per ml and the average pore diameter of the particles is closely controlled and between about 100 A and 1200 A. Actual silanization and antibody immobilization techniques are described in U.S. Pat. No. 3,652,761, cited above.

In the examples below detailed directions are given for preparing the suspensions of porous glass particles, the particle size distributions of which are shown in Table II and the Figures.

EXAMPLES I – IV

About ¼ pound of Corning Code 7407 porousglass particles (550 A average pore diameter, 40/80 mesh, U.S. Standard Sieve) was milled with ½ pound of water in a Rolex "O" vibratory mill using 3 lbs. of alumina cylinders for a vibration time of 30 hours. Then, based on the volume of the slurry obtained from the milling operation, enough HCl ($HNO_3$ can also be used) is added to make the solution 0.8N using a 3/1:acid (vol./wt.) to solid ratio. The acid slurry is then sonicated at 80° C. for 1½ hours.

The slurry is then centrifuged at 5000 RPM for ¼ hour (Model RC2-B Sorvall Centrifuge with a GS-3 rotor, avg. radius, 5 inches) to remove the spent acid. The supernatant liquid is decanted off and discarded.

Then clean dionized water (in the 3/1 ratio) (vol./wt.) is added to the centrifuge sediment and sonicated at greater than 75° C. for 1 hour. The suspension is then centrifuged again at 5000 RPM for 15 minutes and again the supernatant fluid is discarded. The suspending and centrifuging steps are repeated, preferably at least five times. The particles are then suspended in an aqueous solution with sonication. For antibody immobilization, the suspension preferably consists of about 12.5% porous glass particles by weight/volume (mg./ml) of aqueous solution.

Five samples of porous glass particles prepared by the above method are shown in the table where the physical characteristics before and after treatment are compared.

TABLE II

| | Physical Properties Of Porous Glass Samples | | | | | | | |
|---|---|---|---|---|---|---|---|---|
| | Initial (After Milling) | | | Final (After Sedimentation Steps) | | | | |
| Example No. | Average Particle Diameter ($\mu$) | % Distribution $\leq 0.7$ | % Distribution $\geq 3.0$ | Average Particle Diameter ($\mu$) | % Distribution $\leq 0.7$ | % Distribution $\geq 3.0$ | Average Pore Size (Å) | Pore Volume (cc/g) | Surface Area ($m^2/g$) |
| 1* | 2.8 | 0.0 | 37 | 1.5 | 9 | 10 | 640 | 0.56 | 78 |
| 2 | 1.5 | 10.0 | 11 | 1.5 | 7 | 8 | 540 | 0.60 | 64 |
| 3** | 13.5 | 0.0 | 98 | 2.6 | 0 | 10 | 485 | 1.06 | 71 |
| 4 | 1.3 | 14.0 | 3 | 1.5 | 8 | 5 | 600 | 1.0 | 93 |
| 5 | 1.5 | 11.0 | 9 | 1.6 | 7 | 10 | 920 | 1.09 | 164 |

*FIG. 2
**FIG. 1

Figure 2:
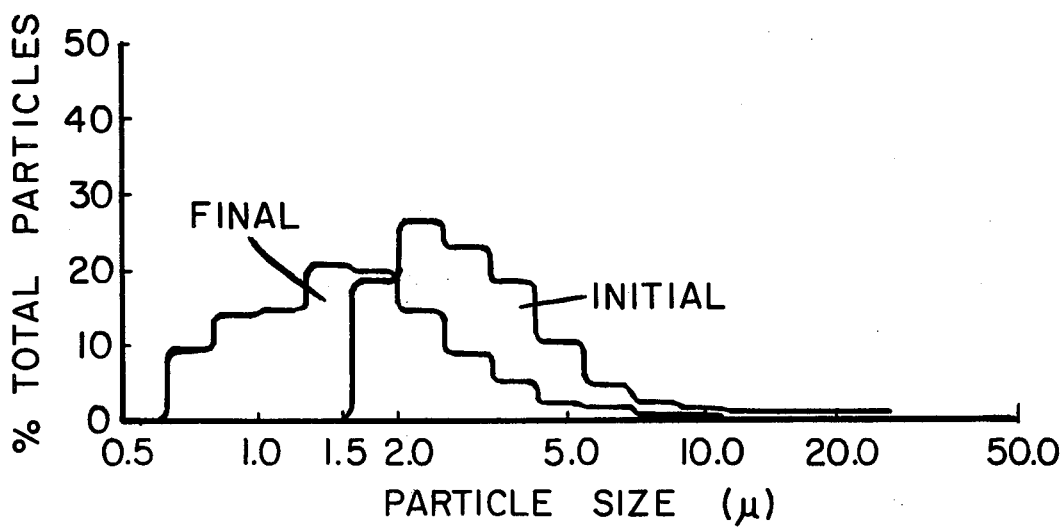

As can be seen in FIGS. 1 and 2, where particle size distribution (before and after the sedimentation steps) is compared for Examples 3 and 1, the critical sedimentation (centrifugation) steps yield a closely controlled particle size for the porous glass particles such that a substantial portion of the particles are between about 0.7 and 3.0$\mu$. Particle size distributions were determined with a Model TA Coulter Counter. Indicated sonication steps were performed with a Crest Ultrasonic Sonicator, Model 4HT-1240-18.

We claim:

1. A method of preparing a suspension of porous glass particles of controlled particle size and useful as antibody carriers in solid phase radioimmunoassay comprising the steps of:

A. milling controlled pore porous glass particles having an average pore diameter between about 100 A and 1200 A to an average particle size of less than about 10 microns;

B. acid-washing the milled particles to remove contaminants and residues;

C. washing the particles to remove any residues from step (B);

D. mixing the washed particles with water to form a first suspension of the particles;

E. subjecting the first suspension to a first sedimentation step to assure removal of particles greater than about 10 microns;

F. subjecting the remaining first suspension to at least one more sedimentation step to sediment particles having an average particle size between about 0.7 and about 3.0 microns; and G. suspending the particles of step (F) in water.

2. The method of claim 1 wherein the porous glass particles of step (A) have an average pore diameter between about 485 A and about 920 A.

3. The method of claim 1 wherein the acid-washing of step (B) is with 0.8 N HCl solution.

4. The method of claim 1 wherein the suspension of step (G) is effected by sonicating the porous glass particles in water.

5. The method of claim 4 wherein the suspension consists of about 50 to about 150 mg of porous glass particles per ml of water.

6. The method of claim 5 wherein the porous glass particles have an average particle size between about 0.7 microns and about 1.7 microns.

7. The method of claim 1 wherein the porous glass particles have a surface area of at least about 20 $m^2/g$.

8. The method of claim 1 wherein the sedimentation of step (E) is accomplished by centrifugation at a relative centrifuge force range of 20 to 80.

9. The method of claim 1 wherein the sedimentation of steo (F) is accomplished by centrifugation at a relative centrifuge force range of 5,000 to 10,000.

10. The method of claim 1 wherein the sedimentation of step (E) is accomplished by centrifugation at a relative centrifuge force range of 20 to 80 and the sedimentation of step (F) is accomplished by centrifugation at a relative centrifuge force range of 5,000 to 10,000.

* * * * *